United States Patent [19]

Kaufman

[11] Patent Number: 4,490,155

[45] Date of Patent: Dec. 25, 1984

[54] MANNICH REACTION PRODUCTS OF DIAMINOPROPANES WITH FORMALDEHYDE AND SALICYCLIC ACIDS

[75] Inventor: Benjamin J. Kaufman, Wappingers Falls, N.Y.

[73] Assignee: Texaco Inc., White Plains, N.Y.

[21] Appl. No.: 524,004

[22] Filed: Aug. 17, 1983

[51] Int. Cl.$^3$ ................................................ C10L 1/22
[52] U.S. Cl. .......................................... 44/71; 44/75; 252/392; 252/403
[58] Field of Search ...................... 44/75, 71; 562/442; 252/392, 403

[56] References Cited

U.S. PATENT DOCUMENTS

| | | | |
|---|---|---|---|
| 2,908,558 | 10/1959 | Brimer | 44/75 |
| 3,116,129 | 12/1963 | Udelhofen | 44/75 |
| 4,038,043 | 7/1977 | Garth | 44/75 |
| 4,083,699 | 4/1978 | Chibnik | 44/75 |
| 4,231,759 | 11/1980 | Udelhofen et al. | 44/75 |

*Primary Examiner*—Y. Harris-Smith
*Attorney, Agent, or Firm*—Robert A. Kulason; Robert Knox, Jr.; Henry W. Archer

[57] ABSTRACT

The Mannich reaction products of certain diaminopropanes with formaldehyde and salicylic acids are potent carburetor detergents and corrosion inhibitors in hydrocarbon fuels, particularly in gasoline.

20 Claims, No Drawings

MANNICH REACTION PRODUCTS OF DIAMINOPROPANES WITH FORMALDEHYDE AND SALICYCLIC ACIDS

BACKGROUND OF THE INVENTION

Field of the Invention

This invention relates to fuels for internal combustion engines and more particularly to the provision of a novel multipurpose additive for such fuels.

As is well known, hydrocarbon fuels have a tendency to form polymeric materials (variously called "gum" or "sludge" or "varnish") in various parts of fuel systems. These resin-like deposits tend to form in the fuel supply lines, fuel filter, carburetor, fuel control injectors, intake manifold and valve stems. Such deposits are objectionable not only because of their effect on mechanical performance but also because they decrease the breathing efficiency in engines of the spark ignition type.

Although each type of fuel is composed essentially of hydrocarbons, the stability characteristics of fuels differ considerably. Thus, typical automotive fuels contain straight and branched chain compounds while aircraft fuels contain a smaller proportion of olefins. Currently, certain types of fuels contain increased amounts of cracked stocks resulting in a higher olefin content and an increased susceptibility to the formation of gum.

Although motor fuels are highly refined products but still contain minor amounts of impurities and water which can cause corrosion in the fuel tank, fuel lines and carburetor of a motor vehicle. Accordingly, commercial motor fuel compositions contain rust inhibitors and/or, antirust agents. Naturally, the economics of providing such fuels are improved if a single multipurpose additive can perform plural functions.

PATENT INFORMATION DISCLOSURE

Prior patents in this field include U.S. Pat. No. 3,296,130 which discloses, an antioxidant and anticorrosion agents, divalent metal salts of salicylaldimine amine acids. Also of interest, is unexamined Japanese patent application JF No. 4019507 which discloses N-alkyl trimethylene diamine salicylate and its use as a corrosion inhibitor in petroleum refining products. Of lesser relevance are coassigned U.S. Pat. Nos. 4,177,041 and 4,321,062.

SUMMARY OF THE INVENTION

The invention provides novel motor fuel additives characterizable by the following generalized structure:

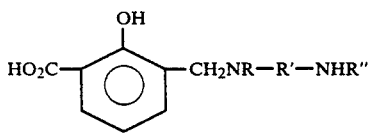

wherein R and R" are the same or different and include hydrogen or an alkyl, aryl, alkenyl, alkaryl or cycloalkyl group having from 8 to 20 carbon atoms such as octyl, decyl, tolyl, and xylyl radicals. When R or R" are alkenyl, they can typically be vinyl, 1-butenyl, and the like. R and R" may be inertly substituted by a nonreactive substituent such as alkyl, aryl, cycloalkyl, or alkoxy which does not affect the properties of the compound. Typical inertly substituted R and R" groups include 2-ethoxylethyl, 2-nitroethyl and p-anilino.

The preferred R and R" groups are alkyl groups containing from 8 to 18 carbon atoms including stearyl (18 carbons); decyl (10 carbons); coco (6–18 carbons); oleyl (12–18 carbons); tallow (12–18 carbons); and soya (14–18 carbons), with R" preferably being hydrogen, R' can be a divalent hydrocarbyl radical including alkylene having about 1 to about 5 carbon atoms, arylene, alkarylene and arylenealkylene having about 6 to about 30 carbon atoms, preferably, R' is a straight chain (lower)alkylene group containing from 1 to 5, more preferably from 1 to 3, and most preferably, 3 carbon atoms.

The invention also provides a gasoline fuel containing an effective detergent and corrosion-inhibiting amount of a compound represented by the above formula, or a mixture of such compounds.

The compounds of the invention are preferably prepared under usual Mannich Reaction conditions by refluxing in an inert solvent, substantially stoichiometric amounts of an N-alkyl-alkylene diamine, paraformaldehyde and a salicylic acid while continuously removing the water of reaction produced as it forms and evaporating the solvent to leave behind a gasoline soluble or dispersible product. This reaction proceeds by replacement of an active hydrogen from the acid, as shown below:

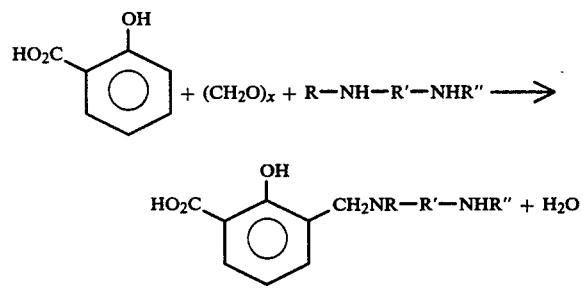

where R, R' and R" are as before and x is 1 to 4.

It will be appreciated that by-products substituted on and/or other ring positions impurities can be coproduced along with the compound or mixture of compounds of the invention in the course of the above reaction. The desired additive compounds can be readily recovered from the reaction product by known methods. However, it is feasible and economical to employ the present compounds as produced without separation or purification.

DISCLOSURE OF BEST MODE

The products of this invention are prepared from starting N-alkyl-alkylene diamine reactants represented by the formula:

in which R, R' and R" are as defined above. As employed herein the term "N-alkyl-alkylene diamine" covers both N-monoalkyl-alkylene diamine and the N-dialkyl-alkylene diamine structure when R' is a (lower)alkyl radical.

The most convenient alkylene diamines to use are those available commercially under the trade name of "Duomeen O" (a product of Armak Co.) wherein the alkyl group is straight chain with an average of 12 to 18 carbon atoms and is attached to the nitrogen through the second carbon in the chain. These are available in mixed forms and when used herein will produce a mixture of products of the above formula.

The starting salicylic acid may be inertly substituted by substituents which are non-reactive within the context of this invention including non-hydrocarbon or polar substituents such as cyano, alkoxy, nitro, halo and which do not affect materially the nature of the salicylic acid. Technical grade paraformaldehyde preferably is used but formaldehyde solutions also are suitable.

The products of the invention can be solids, semi-solids or oils depending upon the nature of the starting materials. For use as additives in fuels, these products must be soluble and/or stably dispersible therein to an extent which allows them to function in their intended manner.

The following example illustrates in non-limiting fashion the best mode of preparing the additives of the invention:

EXAMPLE I

A mixture of 100 g. of N-oleyl-1,3-diaminopropane, paraformaldehyde (13 g), salicylic acid (40 g) and xylene (150 g) was heated to reflux until the water of reaction (17.2 g) was azeotroped away. The xylene was then evaporated leaving an amber colored oil (151 g) as a product. Elemental analysis confirmed the above formula and gave the analytical results which follow.

| | |
|---|---|
| TAN | 76.7 |
| % N | 4.6 |
| TBN | 162.1 |
| SAP# | 95.23; 95.74 |

By proceeding as indicated in the above example, there are obtained with the diamines tabulated below in Table 1, products interchangeable with that of Example 1 within the context of this invention.

TABLE I

| EXAMPLE NO. | DIAMINE |
|---|---|
| 2 | dodecyl-NH-$CH_2$-$CH_2$-$CH_2$-NH-octyl |
| 3 | octyl-NH-$CH_2$-$CH_2$-$CH_2$-NH-octyl |
| 4 | stearyl-NH-$CH_2$-$CH_2$-$CH_2$-NH-lauryl |
| 5 | decyl-NH-$CH_2$-$CH_2$-$CH_2$-$NH_2$ |
| 6 | lauryl-NH-$CH_2$-$CH_2$-$CH_2$-NH-octyl |
| 7 | behenyl-NH-$CH_2$-$CH_2$-$CH_2$-$NH_2$ |
| 8 | cocoyl-NH-$CH_2$-$CH_2$-$CH_2$-$NH_2$ |
| 9 | stearyl-NH-$CH_2$-$CH_2$-$CH_2$-NH-octyl |
| 10 | tallow-NH-$CH_2$-$CH_2$-$CH_2$-$NH_2$ |
| 11 | lauryl-NH-$CH_2$-$CH_2$-$CH_2$-$NH_2$ |
| 12 | myristyl-NH-$CH_2$-$CH_2$-$CH_2$-$NH_2$ |

The detergency of any gasoline suitable for a spark-ignited, internal combustion engine can be improved in the practice of this invention. In general, the base fuel will consist of a mixture of hydrocarbons in the gasoline boiling range i.e., boiling from about 75° to 450° F. The hydrocarbon components can consist of paraffinic, naphthenic, aromatic and olefinic hydrocarbons. This gasoline can be obtained naturally or it can be produced by thermal or catalytic cracking and/or reforming of petroleum hydrocarbons. The base fuel will generally have a Research Octane Number above 85 and up to about 102 with the preferred range being from about 90 to 100.

In general, the additive composition of the invention is added in single or mixture form to a base fuel in a minor amount, i.e., an amount effective to provide corrosion inhibition, deicing properties and carburetor detergency to the fuel composition. The additive is effective in an amount ranging from about 0.002 to 0.5 weight percent based on the total fuel composition. An amount of the neat additive ranging from about 0.01 to 0.03 weight percent is preferred, with an amount from about 0.01 to 0.02 being particularly preferred, the latter amounts corresponding to about 3 to 50 PTB (pounds of additive per 1000 barrels of gasoline) respectively.

The fuel composition of the invention may contain effective amounts of any of the additives normally employed in a motor fuel. For example, the base fuel may be blended with an antiknock compound, such as a methylcyclopentadienyl manganese tricarbonyl or tetraalkyl lead compound, including tetraethyl lead, tetramethyl lead, tetrabutyl lead, and chemical and physical mixtures thereof, generally in a concentration from about 0.025 to 4.0 cc. per gallon of gasoline. The tetraethyl lead mixture commercially available for automotive use contains an ethylene chloride-ethylene bromide mixture as a scavenger for removing lead from the combustion chamber in the form of a volatile lead halide.

The present additives were tested for effectiveness in the carburetor detergency test. This test is run on a Chevrolet V-8 engine mounted on a test stand using a modified four-barrel carburetor. The two secondary barrels of the carburetor are sealed and the feed to each of the primary barrels arranged so that the detergent additive fuel can run in one barrel and the reference fuel run in the other. The primary carburetor barrels were also modified to contain removable aluminum inserts in the throttle plate area so that the deposits formed on the inserts could be conveniently weighed.

In the procedure designed to determine the effectiveness of an additive fuel to remove preformed deposits in the carburetor, the engine is run for a period of time, usually 24 to 48 hours, using the base fuel as the feed to both barrels with engine blow-by circulated to the air inlet of the carburetor. The weight of the deposits on both left and right (L,R) sleeves is determined and recorded. The engine is then cycled for 24 additional hours with a reference fuel being fed to one barrel, additive fuel to the other, and no blow-by to the carburetor air inlet. The reference fuel contains 15 PTB of a carburetor detergent. The inserts are then removed from the carburetor and weighed to determine the difference between the performance of the additive and nonadditive fuels in removing the preformed deposits. After the aluminum inserts are cleaned, they are replaced in the carburetor and the process repeated with the fuels reversed in the carburetor to minimize differences in fuel distribution and barrel construction. The effectiveness of the additive fuel is expressed as the differences (Δ) between deposit removed by the additive fuel and the deposit removed by base fuel. When (Δ) is positive, the additive fuel has removed more deposit than the reference fuel.

The rust inhibiting properties of fuel compositions of the invention were determined in the NACE Test (National Association of Corrosion Engineers) which is a modification of ASTM Rust Test D-665-60 Procedure A. In the NACE Test, a steel spindle is polished with non-waterproof fine emery cloth. The spindle is immersed in a mixture containing 300 cc fuel and 30 cc distilled water and is rotated at 100° F. for 3.5 hours. The spindle is then rated visually to determine the amount of rust formation. A passing result is an average of less than 5% rust.

The compound of Example 1 was tested by the above tests with the results tabulated below in Table II.

TABLE II

1. Chevrolet Carburetor Detergency Test
   at 20 PTB % Δ = +8 vs 20 PTB of commercial additive
2. National Association of Corrosion Engineers (NACE) Test

| PTB | % RUST |
|---|---|
| 10 | Trace, Trace |
| 5 | 1-5, 1-5 |

The compound of Example 1 was also tested on the Waring Blender Emulsion Test which evaluates the tendency of motor gasolines to form an emulsion or haze with various water bottoms and to examine the stability of such haze or emulsion.

In this test, a mixture consisting of 95 percent test gasoline and 5 percent test water is mixed at approximately 13,000 rpm for 10 seconds in an explosion proof Waring blender. The mixture is transferred to a graduated cylinder, and allowed to stand four hours. The appearance of the water layer is observed visually and the haze of the gasoline layer is measured with a haze meter. Readings on this meter of around 100 or less are acceptable.

Comparative results at various pH's are as follows for a 4 hr. Haze Reading

| Waring Blender Emulsion Test | | |
|---|---|---|
| PTB | PH 5 | PH 12 |
| Example 1 Product | 10 | 18 | 110 |

The data of the above test show that the present additive does not cause a water separation problem in a fuel and compare favorably with data obtained with commercial additive packages which do not cause water entrainment problems.

The data of the above tests show that the additive of the invention outperformed the commercial reference additive in the detergency test and that fuels containing same passed the corrosion and Waring Blender tests.

This invention has been described in narrow and broad terms and is understood to be susceptible of many minor modifications which may occur to those skilled in the art. Such modifications are deemed to be within the scope of my invention.

What is claimed is:

1. A composition of matter comprising one or more compounds of the formula:

$$HO_2C-\text{(benzene ring with OH)}-CH_2NRR'NHR''$$

wherein R and R" are the same or different and include hydrogen, alkyl, aryl, alkenyl, alkaryl, and cycloalkyl groups having from about 8 to about 20 carbon atoms; and R' is a divalent hydrocarbyl radical of the group of alkylene having about 1 to about 5 carbon atoms, arylene, alkarylene, and arylenealkylene having about 6 to about 30 carbon atoms.

2. The composition of claim 1, wherein R' is a straight chain (lower)alkylene group having 1 to 5 carbon atoms.

3. The composition of claim 2, wherein R' contains 1 to 3 carbon atoms.

4. The composition of claim 2, wherein R' contains 3 carbon atoms.

5. A composition of matter formed by reacting under Mannich Reaction conditions formaldehyde, a salicylic acid and a N-alkyl-alkylene diamine represented by the formula:

RNH—R'—NHR"

wherein R, R'-and R" are as in claim 1.

6. The composition of claim 5, characterized in that the diamine has the formula:

dodecyl—NH—$CH_2$—$CH_2$—$CH_2$—NH—octyl.

7. The composition of claim 5, wherein said diamine has the formula:

octyl—NH—$CH_2$—$CH_2$—$CH_2$—NH—octyl.

8. The composition of claim 5, wherein said diamine has the formula:

stearyl—NH—$CH_2$—$CH_2$—$CH_2$—NH—lauryl.

9. The composition of claim 5, wherein said diamine has the formula:

decyl—NH—$CH_2$—$CH_2$—$CH_2$—$NH_2$.

10. The composition of claim 5, wherein said diamine has the formula:

lauryl—NH—$CH_2$—$CH_2$—$CH_2$—NH—octyl.

11. The composition of claim 5, wherein said diamine has the formula:

behenyl—NH—$CH_2$—$CH_2$—$CH_2$—$NH_2$.

12. The composition of claim 5, wherein said diamine has the formula:

cocoyl—NH—$CH_2$—$CH_2$—$CH_2$—$NH_2$.

13. The composition of claim 5, wherein said diamine has the formula:

stearyl—NH—$CH_2$—$CH_2$—$CH_2$—NH—octyl.

14. The composition of claim 5, wherein said diamine has the formula:

tallow—NH—$CH_2$—$CH_2$—$CH_2$—$NH_2$.

15. The composition of claim 5, wherein said diamine has the formula:

lauryl—NH—$CH_2$—$CH_2$—$CH_2$—$NH_2$.

16. The composition of claim 5, wherein said diamine has the formula:

myristyl—NH—$CH_2$—$CH_2$—$CH_2$—$NH_2$.

17. In an improved motor fuel comprising a major amount of a mixture of hydrocarbons in the gasoline boiling point range and a combination of additives in an amount sufficient to achieve each additive's function, the improvement whereby said fuel contains a minor effective detergent and corrosion-inhibiting amount of a composition as defined in claim 1.

18. The fuel of claim 17, containing from 0.002 to 0.50 weight percent of said composition.

19. The fuel of claim 17, containing from 0.01 to 0.03 weight percent of said composition.

20. The fuel of claim 17, containing from 0.01 to 0.02 weight percent of said composition.

* * * * *